(12) United States Patent
Jansson et al.

(10) Patent No.: US 10,835,868 B2
(45) Date of Patent: Nov. 17, 2020

(54) FILTER DEVICE, SYSTEM AND METHOD FOR FILTRATION OF FLUIDS

(71) Applicant: Gambro Lundia AB, Lund (SE)

(72) Inventors: Olof Jansson, Vellinge (SE); Björn Ericson, Lund (SE)

(73) Assignee: GAMBRO LUNDIA AB, Lund (SE)

(*) Notice: Subject to any disclaimer, the term of this patent is extended or adjusted under 35 U.S.C. 154(b) by 8 days.

(21) Appl. No.: 16/001,246

(22) Filed: Jun. 6, 2018

(65) Prior Publication Data

US 2018/0280884 A1 Oct. 4, 2018

Related U.S. Application Data

(63) Continuation of application No. PCT/EP2016/080487, filed on Dec. 9, 2016.

(30) Foreign Application Priority Data

Dec. 11, 2015 (EP) .................................... 15199582

(51) Int. Cl.
*B01D 63/04* (2006.01)
*A61M 1/16* (2006.01)
(Continued)

(52) U.S. Cl.
CPC ............... *B01D 63/04* (2013.01); *A61M 1/16* (2013.01); *A61M 1/1621* (2014.02);
(Continued)

(58) Field of Classification Search
CPC .... A61M 1/16; A61M 1/1621; A61M 1/1627; A61M 1/34; A61M 1/3403;
(Continued)

(56) References Cited

U.S. PATENT DOCUMENTS

| 5,882,516 A | 3/1999 | Gross et al. |
| 5,891,338 A | 4/1999 | Bell et al. |

(Continued)

FOREIGN PATENT DOCUMENTS

| EP | 0264695 | 4/1988 |
| EP | 0791368 | 8/1997 |

(Continued)

OTHER PUBLICATIONS

Boschetti-de-Fierro, Adriana et al. "Extended Characterization of a New Class of Membranes for Blood Purification: The High Cut-Off Membranes" The International Journal of Artificial Organs May 2013; 36(7); pp. 455-463.

(Continued)

*Primary Examiner* — Dirk R Bass
(74) *Attorney, Agent, or Firm* — Jason H. Vick; Sheridan Ross, PC (57) ABSTRACT

A filter device (10) for filtration of fluids, in particular for the dialysis of blood. The filter device (10) comprises a housing (12) having a first end (14) and a second end (16) and defining a fluid chamber (18) extending between the first end (14) and the second end (16). The filter device (10) further comprises a first lid (20) provided at the first end (14) of the housing (12) and comprising a first fluid port (22), a first compartment (24), a second compartment (26) and a first internal separating wall (28) separating the first compartment (24) from the second compartment (26). The filter device (10) further comprises a second lid (30) provided at the second end (16) of the housing (12) and comprising a second fluid port (32), a third fluid port (33), a third compartment (34), a fourth compartment (36) and a second internal separating wall (38) separating the third compartment (34) from the fourth compartment (36). The filter device (10) further comprises a plurality of hollow fibers (Continued)

(40) arranged within the housing (12), wherein each of the plurality of hollow fibers (40) comprises a semi-permeable membrane and defines a fluid channel extending longitudinally through an interior of the respective hollow fiber (40). The filter device (10) further comprises a first sealing means (42) which separates the fluid chamber (18) from the first and the second compartment (24, 26), the first sealing means (42) having a first longitudinal end facing away from the second lid (30). The filter device (10) further comprises a second sealing means (46) which separates the fluid chamber (18) from the third and the fourth compartment (34, 36), the second sealing means (46) having a second longitudinal end facing away from the first lid (20). Still further, the filter device (10) comprises a fourth fluid port (50) and a fifth fluid port (52) both provided at the fluid chamber (18) and located between the first longitudinal end of the first sealing means (42) and the second longitudinal end of the second sealing means (46).

16 Claims, 6 Drawing Sheets (51) Int. Cl.
*A61M 1/34* (2006.01)
*B01D 61/58* (2006.01)
*B01D 61/28* (2006.01)
*B01D 61/30* (2006.01)

(52) U.S. Cl.
CPC ............ *A61M 1/1627* (2014.02); *A61M 1/34* (2013.01); *A61M 1/3403* (2014.02); *A61M 1/3437* (2014.02); *B01D 61/28* (2013.01); *B01D 61/30* (2013.01); *B01D 61/58* (2013.01); *B01D 2313/04* (2013.01); *B01D 2313/21* (2013.01)

(58) Field of Classification Search
CPC ............ A61M 1/3437; B01D 2313/04; B01D 2313/21; B01D 61/28; B01D 61/30; B01D 61/58; B01D 63/04
See application file for complete search history.

(56) References Cited

U.S. PATENT DOCUMENTS

| | | | |
|---|---|---|---|
| 7,622,041 B2 | 11/2009 | Dannenmaier et al. | |
| 2002/0190000 A1 | 12/2002 | Baurmeister | |
| 2005/0131331 A1* | 6/2005 | Kelly | A61M 1/3403 604/4.01 |
| 2007/0181488 A1* | 8/2007 | Dannenmaier | B01D 61/30 210/450 |
| 2009/0076433 A1* | 3/2009 | Folden | A61M 1/3643 604/4.01 |
| 2013/0020250 A1 | 1/2013 | Keller et al. | |
| 2015/0314057 A1 | 11/2015 | Labib et al. | |

FOREIGN PATENT DOCUMENTS

| | | |
|---|---|---|
| EP | 1466657 | 10/2004 |
| EP | 2113298 | 11/2009 |
| JP | 3-86218 A | 4/1991 |
| JP | 7-68135 A | 3/1995 |
| WO | WO 01/47580 | 7/2001 |
| WO | WO 2008/046779 | 4/2008 |
| WO | WO 2013/010666 | 1/2013 |

OTHER PUBLICATIONS

International Search Report for International Application No. PCT/EP2016/080487, dated Feb. 16, 2017.
Written Opinion for International Application No. PCT/EP2016/080487, dated Feb. 16, 2017.
Chinese Office Action (Including Translation) for Chinese Application No. 201680072432.0, dated Jul. 2, 2020.

* cited by examiner

FILTER DEVICE, SYSTEM AND METHOD FOR FILTRATION OF FLUIDS

CROSS REFERENCES TO RELATED APPLICATIONS

This application is a continuation of international patent application PCT/EP2016/080487, filed on Dec. 9, 2016 designating the U.S., which international patent application has been published in English language and claims priority from European patent application EP 15199582.6, filed on Dec. 11, 2015. The entire content of this priority application is incorporated herein by reference.

FIELD OF THE INVENTION

This disclosure relates to a filter device, system and method for filtration of fluids.

BACKGROUND OF THE INVENTION

Filter devices having hollow fibers are used, for example, in the area of dialysis for a wide variety of purposes. Such filters may thus also be referred to as dialysers, these being used for example in haemodialysis (HD), in which blood is directed into and along the inside of the semi-permeable membranes of the hollow fibers while dialysis fluid is directed around the outside of the hollow fibers. Various convection and diffusion processes may thereby take place across the membranes of the hollow fibers. These processes serve, for example, to purify and to remove excess fluid, in particular waste products such as urinary excreted substances, from the blood. Additionally, the electrolyte concentration in the blood can be adjusted and/or normalized, and buffers such as bicarbonate or acetate can be added to the blood. The HD process is effective at removing substances having a low molecular weight.

The above-mentioned filter devices may generally also be employed in so-called haemofiltration (HF), in which a substitution fluid is added to the blood. According to this process, the blood is directed through the inside of the hollow fibers, although in this case no dialysis fluid is normally passed around the outside of the fibers. Here, excess fluids, in particular plasma water as well as waste products, are removed from the blood by means of a pressure difference across the semi-permeable membranes of the hollow fibers. The substitution fluid can be added either pre or post the filtration unit. This is regarded as, respectively, pre or post dilution HF treatment.

A further application for the present type of filter device includes haemodiafiltration (HDF): a combination of HD and HF, in which dialysate flows on the outside of the hollow fibers while blood flows on the inside of the hollow fibers and, at the same time, a pressure gradient exists across the semi-permeable membrane, i.e. between the inside and the outside of the hollow fibers. Infusion fluid may be added to the blood either prior to or after the filtration. This process can result in a higher filtration rate and is especially effective at removing substances having a low and middle molecular weight.

U.S. Pat. No. 7,622,041 B2 discloses a filter device comprising a housing and two end-caps, one arranged at each end of the housing. The housing comprises a longitudinally extending tubular wall having two opposed ends. A fluid port is provided at each of the two opposed ends for introducing blood from a patient and removing the blood after being filtered. Two additional fluid ports are arranged each on one of the two end-caps, the two additional fluid ports being used for introducing and removing a dialysis fluid. A plurality of hollow fibers is arranged within the housing for directing the introduced blood from one end-cap to the other end-cap.

Although the filter device known from the above-mentioned prior art is able to both filter the blood and purify infusion fluids, the device has a comparatively complicated design by including one or more internal walls inside the housing in order to divide the inner space of the housing into two or more compartments.

SUMMARY OF THE INVENTION

It is an object to provide a filter device, system and method for filtration of fluids which enable easy production of useful fluids such as infusion fluids and/or substitution fluids, easy priming and/or rinsing off process while maintaining the safety and efficiency of filtration.

According to a first aspect, a system for filtration of fluids, comprising a filter device for filtration of fluids is presented, wherein said filter device comprises:

a housing having a first end and a second end and defining a fluid chamber extending between the first end and the second end;

a first lid provided at the first end of the housing and comprising a first fluid port, a first compartment, a second compartment and a first internal separating wall separating the first compartment from the second compartment;

a second lid provided at the second end of the housing and comprising a second fluid port, a third fluid port, a third compartment, a fourth compartment and a second internal separating wall separating the third compartment from the fourth compartment;

a plurality of hollow fibers arranged within the housing, wherein each of the plurality of hollow fibers comprises a semi-permeable membrane and defines a fluid channel extending longitudinally through an interior of the respective hollow fiber, wherein the fluid channel of each hollow fiber is encompassed by the semi-permeable membrane of the respective hollow fiber;

a first sealing means which separates the fluid chamber from the first and the second compartment, the first sealing means having a first longitudinal end facing away from the second lid;

a second sealing means which separates the fluid chamber from the third and the fourth compartment, the second sealing means having a second longitudinal end facing away from the first lid;

a fourth fluid port and a fifth fluid port both provided at the fluid chamber and located between the first longitudinal end of the first sealing means and the second longitudinal end of the second sealing means;

wherein the first fluid port is arranged at the first compartment, wherein the second fluid port is arranged at the third compartment, wherein the third fluid port is arranged at the fourth compartment, wherein the plurality of hollow fibers comprise a first group of fibers and a second group of fibers, wherein each hollow fiber of the first group of fibers extends from the first compartment through the fluid chamber to the third compartment and fluidly connects the first compartment with the third compartment via the fluid channels extending through the interior of each hollow fiber of the first group of fibers, and wherein each hollow fiber of the second group of fibers extends from the second compartment through the fluid chamber to the fourth compartment and fluidly connects the second compartment with the fourth compartment via the fluid channels extending through the interior of each hollow fiber of the second group of fibers, and wherein the fourth and the fifth fluid port are fluidly connected to one another and both in fluidic communication with an exterior of both the hollow fibers of the first and the second group of fibers via the fluid chamber and wherein the system further comprises a substitution fluid line which is configured to be switchable between a pre-dilution mode, in which the third fluid port is fluidly connected to the first fluid port of the filter device, and a post-dilution mode, in which the third fluid port is fluidly connected to the second fluid port of the filter device, the substitution fluid line being arranged outside the housing of the filter device.

According to a second aspect, a method for filtration of fluids using the aforementioned filter device is presented, the method comprising the steps of:

introducing a first fluid into the filter device through the first fluid port;

directing the first fluid from the first lid to the second lid via the first compartment, the fluid channels in the interior of the first group of hollow fibers, and the third compartment;

draining the first fluid from the filter device through the second fluid port;

introducing a second fluid into the filter device through the fourth fluid port;

draining a first part of the second fluid from the filter device through the fifth fluid port;

filtering a second part of the second fluid by guiding it from the fourth fluid port via the fluid chamber to the exterior of the second group of hollow fibers, through the semi-permeable membranes of the second group of hollow fibers into the fluid channels in the interior of the second group of hollow fibers and to the third fluid port; and draining the filtered second part of the second fluid from the filter device through the third fluid port.

Refinements are defined in the dependent claims. It shall be understood that the claimed system and method have similar and/or identical refinements.

The first fluid port and the second fluid port are configured to introduce a first fluid from the exterior into the filter device and to remove the introduced first fluid after filtration. For instance, the first fluid port functions as a fluid inlet, whereas the second fluid port functions as a fluid outlet.

Subsequently, the introduced first fluid reaches the first compartment that is in direct fluid connection to the first fluid port. The first fluid then enters the internal fluid channel of the first group of hollow fibers and may flow across the fluid chamber before arriving at the second lid. After reaching the third compartment of the second lid, which is in direct fluid connection to the second open end of the first group of hollow fibers as well as to the second fluid port, the first fluid may be removed from the filter device through the second fluid port.

Further, a second fluid may be introduced into the filter device through the fourth fluid port and, after flowing inside the fluid chamber, removed from the filter device through the fifth fluid port. The fourth fluid port may be arranged closer to the second end of the filter device than the fifth fluid port.

Since the first compartment is separated from the second compartment of the first lid, no fluid can flow between the first and second compartment. For the same reason, no fluid can flow between the third and fourth compartment of the second lid.

The first sealing means defines a longitudinal end of the first and second compartment facing the fluid chamber. The second sealing means defines a longitudinal end of the third and fourth compartment facing the fluid chamber. The first and second group of hollow fibers are connected to the first and second lid via the first and second sealing means, respectively. The first and second sealing means are preferably configured to achieve a sealing effect such that only fluids flowing along the internal fluid channels of the first and second group of hollow fibers may enter the respective compartments of the first and second lid coming from the central fluid chamber. In other words, no fluid may directly enter from the central fluid chamber one or the respective compartments of the first and second lid through the sealing means.

Dialysis-type treatments can therefore be performed using the filter device. In this case, blood from a patient is introduced into the filter device at the first fluid port as the first fluid, wherein a dialysis fluid is introduced into the filter device at the fourth fluid port as the second fluid mentioned above.

In this way, blood introduced into the filter device via the first fluid port enters the first compartment of the first lid, then flows through the internal fluid channels of the first group of hollow fibers to the third compartment of the second lid, such that it may finally exit the filter device via the second fluid port. Since the hollow fibers of the first group comprise each a semi-permeable wall, various convection and diffusion processes may take place across these semi-permeable membranes. Such processes serve to purify and replenish the blood and to remove excess fluid from the blood.

The expression "the fourth and fifth fluid port are in fluidic communication via the fluid chamber to the exterior of the plurality of hollow fibers" means that a fluid entering the fourth or the fifth fluid port may reach the exterior of the plurality of hollow fibers via the fluid chamber. In particular, since the fourth and fifth fluid port are in fluidic communication via the fluid chamber to the exterior/outside of each of the first group of hollow fibers, the dialysis fluid introduced into the fluid chamber, e.g. through the fourth fluid port, can reach the outer surface of the semi-permeable membranes of the first group of hollow fibers. This facilitates removal of excess fluid and diffusion of waste products from the internal fluid channels of the first group of hollow fibers through the semi-permeable membranes into the space within the fluid chamber outside of the first group of hollow fibers. The excess fluid and waste products can be removed from the fluid chamber, e.g. through the fifth fluid port, together with the dialysis fluid.

A substitution fluid, which may e.g. comprise water, can be added either pre or post the filtration unit.

During haemodiafiltration a certain amount of plasma water is removed from the patient's blood. This lack of plasma water needs to be replaced. The herein presented device allows for replacing the plasma water based on a filtration of dialysis fluid. The dialysis fluid is introduced through the fourth fluid port into the filter device. Since the fourth and the fifth fluid port are both fluidly connected not only to the exterior/outside of each of the first group of hollow fibers, but also to the exterior/outside of each of the second group of hollow fibers via the fluid chamber, the useful substances contained in the introduced dialysis fluid may permeate the internal fluid channels of the second group of hollow fibers through the semi-permeable membranes (from the outside to the inside of the hollow fibers) such that the dialysis fluid is thereby filtered. This filtered dialysis fluid including the useful substances can then be used as substitution fluid that replaces the plasma water extracted from the patient during haemodiafiltration. It may enter the fourth compartment of the second lid and exit the filter device through the third fluid port, which is in direct fluid connection to the fourth compartment.

In this way, the filter device serves as a filter for producing, purifying and/or filtering useful fluids, e.g. substitution fluids, infusion fluids and/or buffer fluids, based on the second fluid, e.g. the dialysis fluid. Advantageously, producing substitution fluids is possible even without providing an additional filter, since the filter device already fulfills the function of such an additional filter, i.e. to filter the useful fluids from the second fluid, e.g. the dialysis fluid.

The herein presented system and method are also advantageous since producing, purifying and/or filtering the useful fluids based on the second fluid is possible without providing a wall inside the fluid chamber to separate the first group of hollow fibers from the second group of hollow fibers. Whilst such a wall may generally be provided, it is not necessary to do so in order to produce and/or to purify the useful fluids.

The fluid chamber is preferably formed as a single-compartment-chamber to accommodate both the first and second group of hollow fibers without a wall in between them. Also, the second fluid introduced through the fourth fluid port can reach both the first and the second group of hollow fibers before exiting the filter device through the fifth fluid port.

In a preferable embodiment, the fourth and the fifth fluid port are in direct fluid connection to the fluid chamber, the direct fluid connection being located between the first longitudinal ends of the first sealing means and the second longitudinal ends of the second sealing means.

In this way, the openings of the fourth and fifth fluid port, through which fluid may flow directly between the respective fluid port and the fluid chamber, are located within the first longitudinal end of the first sealing means and the second longitudinal end of the second sealing means.

This ensures that fluids that are introduced into the fluid chamber through the fourth and/or fifth fluid port are not able to flow into the first and second compartment of the first lid or the third and fourth compartment of the second lid. The afore-mentioned openings of the fourth and the fifth fluid ports are preferably arranged to extend beyond a longitudinal end of the first and second sealing means facing the fluid chamber in the longitudinal direction.

In another preferable embodiment, the fluid chamber is spatially confined by an inner, tubular wall of the housing, the first sealing means and the second sealing means.

In this way, the fluid chamber is confined circumferentially by the inner tubular wall of the housing, wherein the fluid chamber is confined longitudinally by the first sealing means and the second sealing means, in particular by the longitudinal ends of the first and second sealing means facing towards the fluid chamber.

In another preferable embodiment, the first compartment is fluidly isolated from the second compartment by means of the first sealing means and the first internal separating wall, and/or wherein the third compartment is fluidly isolated from the fourth compartment by means of the second sealing means and the second internal separating wall.

In another preferred embodiment, the first and/or the second sealing means comprises a potting compound for receiving the first and/or the second group of hollow fibers.

Potting compounds are advantageous for both providing an anchoring means to secure the hollow fibers and/or sealing the compartments of the respective lid against the fluid chamber.

In another preferable embodiment, the filter device further comprises a sixth fluid port arranged at the second compartment of the first lid, the sixth fluid port being closed by a closing means.

In this way, the filter device can be build symmetrically with respect to a middle surface perpendicular to the longitudinal direction of the housing. This enables to use the different fluid ports at both ends of the housing as fluid inlet or outlet.

In another preferred embodiment, the first group of hollow fibers comprises more fibers than the second group of hollow fibers. According to exemplary embodiments, the first group of hollow fibers may comprise at least 70%, at least 80%, or at least 90% of the hollow fibers arranged within the filter device.

In this way, the filtration rate is increased by directing the first fluid through the first group of hollow fibers. In particular, the dialysis-type treatments are more efficient.

In another preferred embodiment, the fluid chamber has at least a part having a circular-cylindrical shape.

This is advantageous regarding a symmetric design of the filter device so that it can be used to direct fluids in either direction along the fluid chamber. Further, a cylindrical shaped fluid chamber is relatively easy to form compared to irregularly shaped chambers.

The system for filtration of fluids is advantageous for filtering the second fluid introduced into the filter device through the fourth or the fifth fluid port and thereby produce a substitution fluid from the filtered second fluid, wherein said substitution fluid can be added to the treated blood of the patient to compensate for the typical removal of plasma water from the patient's blood that occurs during haemodiafiltration. Thus, no extra/additional source of substitution fluid needs to be provided, since the system enables to filter the dialysis fluid to produce substitution fluid.

In a preferable embodiment, the system further comprises: (i) an arterial line for fluidly connecting an arterial side of a patient access to the first fluid port of the filter device, (ii) a venous line for fluidly connecting a venous side of the patient access to the second fluid port of the filter device, (iii) a first pump for pumping a first fluid into the first fluid port and/or for draining the first fluid from the second fluid port of the filter device, and (iv) a second pump for pumping a second fluid into the fourth fluid port and/or for draining the second fluid from the fifth fluid port of the filter device.

The system advantageously enables the type of treatment, in which blood is taken from an arterial side of a patient access and given to a venous side of the patient access after filtration by the filter device. Further, the flow of the second fluid, in particular dialysis fluid, is assisted by the second pump.

In another preferred embodiment, the substitution fluid line is fluidly connected to the arterial line and/or the venous line.

When the substitution fluid line is fluidly connected to the arterial line, the filter device can be used in a pre-dilution mode. When the substitution fluid line is fluidly connected to the venous line, the filter device can be used in a post-dilution mode.

In another preferred embodiment, the system further comprises a further line for fluidly connecting the second fluid port of the filter device to a waste handling unit and/or a waste bag.

In this way, the system can be used to perform priming and/or rinse-back of the filter device, wherein waste fluid removed from the filter device can be selected and/or further processed in a secure way, thereby advantageously minimizing impacts to the environment.

The above-mentioned features and those yet to be explained in the following text are usable not only in the combination given in each case but also in other combinations or on their own, without departing from the spirit and scope of the present disclosure

DETAILED DESCRIPTION OF THE INVENTION

Figure 6:
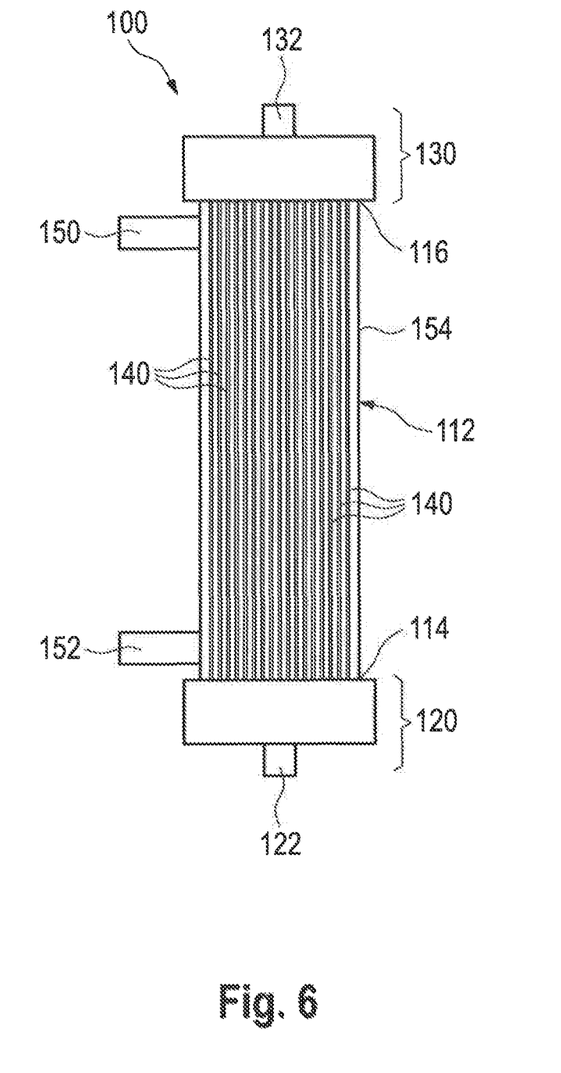
FIG. 6 shows schematically a filter device according to the prior art.

A filter device 100 for filtration of fluids, in particular for dialysis-type treatments generally known from the prior art is schematically shown in FIG. 6. The filter device 100 comprises a housing 112 and two end-caps 120, 130. The housing 112 comprises a longitudinally extending tubular wall 154 having two opposed ends 114, 116, wherein the end-caps 120, 130 are arranged each at one of both ends 114, 116. A fluid port 122, 132 is provided at each of the two end-caps 120, 130 for introducing blood from a patient and removing the blood after being filtered. Two additional fluid ports 150, 152 are arranged each at one of the two ends 114, 116. The two additional fluid ports 150, 152 are used for introducing and removing a dialysis fluid. A plurality of hollow fibers 140 are arranged within a chamber of the housing 112 for directing the introduced blood from one end-cap 120 to the other end-cap 130.

Figure 1:
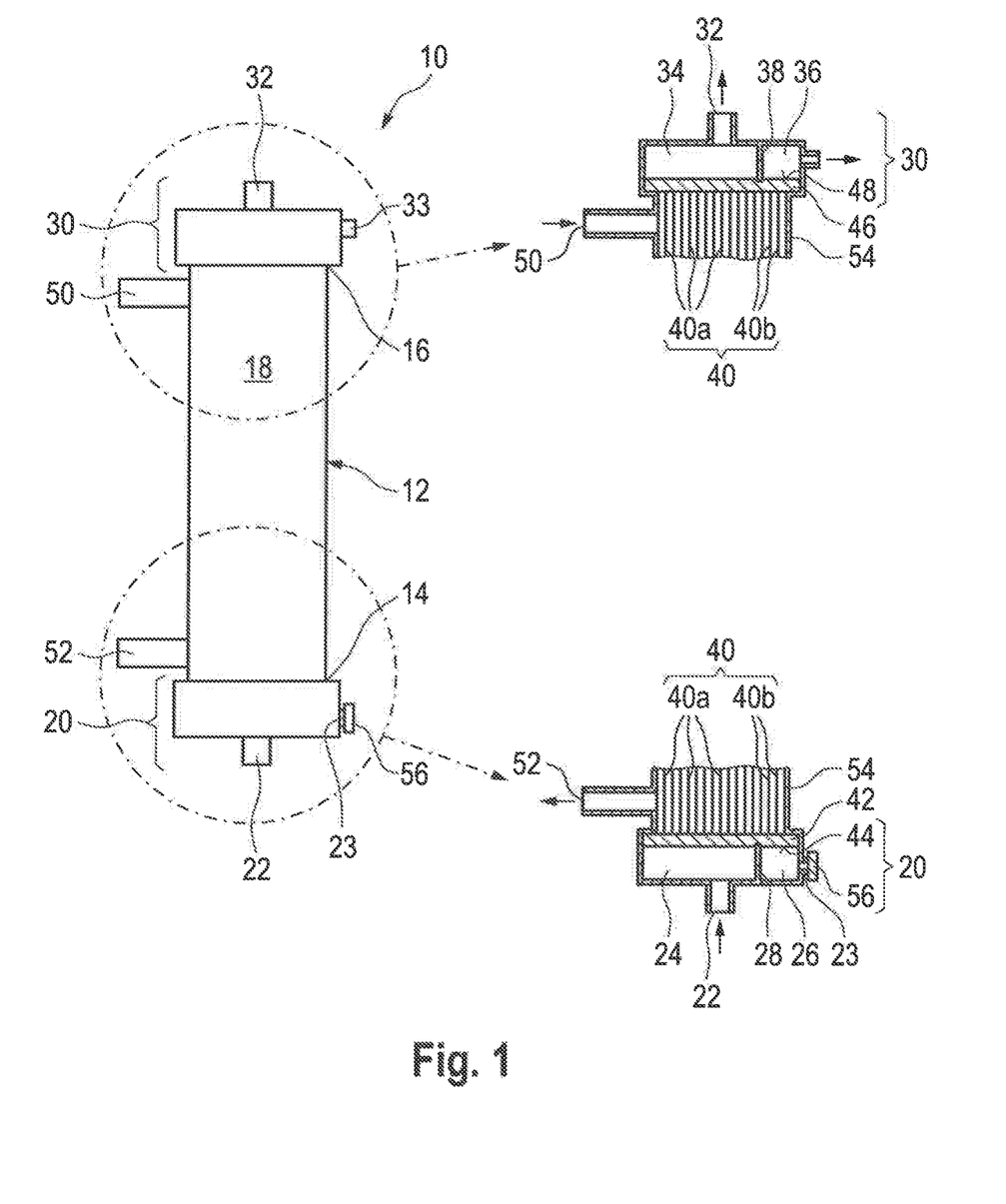
FIG. 1 shows schematically a filter device according to an embodiment.

FIG. 1 shows a filter device 10 which may be used for treating blood (as in a "regular" dialyser) and for (additionally) filtering dialysis fluid. The filter device 10 comprises a housing 12 having a first end 14 and a second end 16 and defines a fluid chamber 18 extending between the first end 14 and the second end 16. As shown in FIG. 1, the fluid chamber 18 preferably has a substantially circular-cylindrical shape.

A first lid 20 is provided at the first end 14 of the housing 12 and comprises a first fluid port 22, a first compartment 24, a second compartment 26 and an internal separating wall 28 separating the first compartment 24 from the second compartment 26. Similarly, a second lid 30 is provided at the second end 16 of the housing 12 and comprises a second fluid port 32, a third compartment 34, a fourth compartment 36 and an internal separating wall 38 separating the third compartment 34 from the fourth compartment 36.

A plurality of hollow fibers 40 are arranged within the housing 12, each of the fibers 40 defining an internal fluid channel extending longitudinally through an interior of the respective hollow fiber. Each fiber comprises a semi-permeable membrane which sidely confines the respective internal fluid channel. The semi-permeable membrane is preferably configured to allow substances, whose size is below a threshold size, to enter the internal fluid channel from exterior of the fiber and/or to exit the internal fluid channel to the exterior of the fiber.

A first sealing means 42 is provided at the first end 14 of the housing 12 for separating the fluid chamber 18 from the first and the second compartment 24, 26. The first sealing means 42 has a first longitudinal end 44 facing away from the second lid 30. Further, a second sealing means 46 is provided at the second end 16 for separating the fluid chamber 18 from the third and the fourth compartment 34, 36, the second sealing means 46 having a second longitudinal end 48 facing away from the first lid 20.

The filter device 10 further comprises a fourth fluid port 50 and a fifth fluid port 52, both being provided at the fluid chamber 18 and located between the first longitudinal end 44 of the first sealing means 42 and the second longitudinal end 48 of the second sealing means 46.

The first fluid port 22 is arranged at the first compartment 24, thereby allowing a direct fluid connection to the first compartment 24. The second fluid port 32 is arranged at the third compartment 34, thereby allowing a direct fluid connection to the third compartment 34. The third fluid port 33 is arranged at the fourth compartment 36, thereby allowing a direct fluid connection to the fourth compartment 36.

The plurality of hollow fibers 40 comprise a first group of fibers 40a and a second group of fibers 40b. Each hollow fiber of the first group 40a extends from the first compartment 24 through the fluid chamber 18 to the third compartment 34, wherein each hollow fiber of the second group 40b extends from the second compartment 26 through the fluid chamber 18 to the fourth compartment 36.

The first and second group of hollow fibers 40a, 40b extend each from a first open end to a second open end. The first open ends are each received by the first sealing means 42. The second open ends are each received at the second sealing means 46. The first and second sealing means 42, 46 are here each provided as a potting compound, into which the fibers 40a, 40b extend. In FIG. 1, it is shown that the two sealing means 42, 46 are arranged within the first and second lid 20, 30, respectively. This is, however, only exemplary. In general, at least one of the two sealing means 42, 46 may be arranged outside of the respective lid towards the center of the housing 18.

The first compartment 24 is in direct fluid connection to the internal fluid channels of the first group of hollow fibers 40a at their first open ends. The third compartment 34 is in direct fluid connection to the internal fluid channels of the first group of hollow fibers 40a at their second open ends. Similarly, the second compartment 26 is in direct fluid connection to the internal fluid channels of the second group of hollow fibers 40b at their first open ends. The fourth compartment 36 is in direct fluid connection to the internal fluid channels of the second group of hollow fibers 40b at their second open ends.

The fourth and the fifth fluid port 50, 52 are fluidly connected to one another and in fluid communication with the exterior side of the plurality of hollow fibers 40 via the fluid chamber 18. This means that a fluid that is introduced to one of the fourth and the fifth fluid port 50, 52 is able to reach the other of these two fluid ports via the fluid chamber 18. Also, a fluid that is introduced to one of these two fluid ports is able to reach the outer surface of the semi-permeable membranes of the both the first group and the second group 40a, 40b of hollow fibers.

The first fluid port 22 and the second fluid port 32 are configured for introducing a first fluid from the exterior into the filter device 10 and for removing the introduced first fluid after filtration. Preferably, the first fluid port 22 functions as a fluid inlet, wherein the second fluid port 32 functions as a fluid outlet.

The introduced first fluid subsequently reaches the first compartment 24 that is in direct fluid connection to the first fluid port 24, as shown in FIG. 1. The first fluid then enters the internal fluid channel of the first group of hollow fibers 40a and may flow across the fluid chamber 18 before arriving at the second lid 30. After reaching the third compartment 34 of the second lid 30, which is in direct fluid connection to the second open end of the first group of hollow fibers 40a as well as to the second fluid port 32, the first fluid may be removed from the filter device 10 through the second fluid port 32.

Further, a second fluid may be introduced into the filter device 10 through the fourth fluid port 50 and, after flowing inside the fluid chamber 18, removed from the filter device 10 through the fifth fluid port 52. The fourth fluid port 50 may be arranged closer to the second end 16 of the filter device 10 than the fifth fluid port 52.

Since the first compartment 24 is separated from the second compartment 26 of the first lid 20, no fluid can flow between the first and second compartment 24, 26. For the same reason, no fluid can flow between the third and fourth compartment 34, 36 of the second lid 30.

The first sealing means 42 defines a longitudinal end of the first and second compartment 24, 26 facing the fluid chamber 18. The second sealing means 46 defines a longitudinal end of the third and fourth compartment 34, 36 facing the fluid chamber 18. The first and second group of hollow fibers 40a, 40b are connected to the first and second lid 20, 30 via the first and second sealing means 42, 46, respectively.

Dialysis-type treatments can therefore be performed using the filter device 10. In this case, blood from a patient may be introduced into the filter device 10 as the first fluid, wherein a dialysis fluid may be introduced into the filter device 10 as the second fluid.

In this way, blood introduced through the first fluid port 22 flows in the internal fluid channels of the first group of hollow fibers 40a through the fluid chamber 18 of the filter device 10. Since the hollow fibers 40a of the first group comprise each a semi-permeable membrane, various convection and diffusion processes may therefore take place across these semi-permeable membranes. Such processes serve to purify and replenish the blood and to remove excess fluids from the blood.

In particular, since the fourth and fifth fluid port 50, 52 are in fluidic communication with the first group of the hollow fibers 40a via the fluid chamber 18, the dialysis fluid (second fluid) introduced into the fluid chamber 18, e.g. through the fourth fluid port 50, can reach the outer surface of the semi-permeable membranes of the first group of hollow fibers 40a. This facilitates removal of excess fluid and diffusion of waste products from the internal fluid channels of the first group of hollow fibers 40a through their semi-permeable membranes into the exterior of these fibers 40a within the fluid chamber 18. The excess fluid and waste products can be removed from the fluid chamber 18, e.g. through the fifth fluid port 52, together with the dialysis fluid.

The blood that is to be introduced into the filter device 10 may be conditioned using a substitution fluid, an infusion fluid or a buffer (e.g. bicarbonate, acetate, etc.). The substances forming the substitution fluid, the infusion fluid or the buffer fluid contained in the introduced blood may therefore diffuse from within the internal fluid channels of the first group of hollow fibers 40a through the semi-permeable membrane into the exterior of these hollow fibers 40a and finally be removed from the filter device 10 through the fifth fluid port 52.

The second fluid (e.g. the dialysis fluid) is introduced through the fourth fluid port 50 into the filter device 10. Since the fourth and the fifth fluid port 50, 52 are both in fluidic communication with the second group of fibers 40b via the fluid chamber 18, the useful substances contained in the introduced second fluid may permeate into the internal fluid channels of the second group of hollow fibers 40b through the semi-permeable membranes of these fibers 40b such that the dialysis fluid is thereby filtered. This filtered dialysis fluid can then be used as substitution fluid that replaces the plasma water extracted from the patient during haemodiafiltration. It may enter the fourth compartment 36 of the second lid 30 and exit the filter device 10 through the third fluid port 33, which is in direct fluid connection to the fourth compartment 36.

In this way, the filter device 10 serves as a filter for producing useful fluids, e.g. substitution fluids, infusion fluids and/or buffer fluids, based on the second fluid, e.g. the dialysis fluid. Advantageously, producing substitution fluids is possible even without providing a wall inside the fluid chamber 18 to separate the first group of hollow fibers from the second group of hollow fibers. Without the presence of such a wall, the fluid chamber 18 is formed as a single-compartment-chamber to accommodate both the first and second group of hollow fibers 40a, 40b. Also, the second fluid introduced through the fourth fluid port 50 can reach both the first and second group of hollow fibers 40a, 40b before being removed from the filter device 10 through the fifth fluid port 52.

Preferably, the fourth and the fifth fluid port 50, 52 are in direct fluid connection to the fluid chamber 18, the direct fluid connection being located only between the first longitudinal end 44 of the first sealing means 42 and the second longitudinal end 48 of the second sealing means 46. In this way, the fourth and the fifth fluid port 50, 52 are fluidly separated from all the compartments 24, 26, 34, 36 at both lids 20, 30. More preferably, the fourth and fifth fluid port 50, 52 are arranged completely away from the first and second lid 20, 30 and/or from the first and second sealing means 42, 46.

As shown in the preferable embodiment of FIG. 1, the fluid chamber 18 is sidely or circumferentially confined by a tubular wall 54 of the housing 12 and longitudinally confined by the first sealing means 42 and the second sealing means 46. Further, the first compartment 24 is fluidly isolated from the second compartment 26 by means of the first sealing means 42 and the first internal separating wall 28, wherein the third compartment 34 is fluidly isolated from the fourth compartment 36 by means of the second sealing means 46 and the first internal separating wall 38.

The filter device shown in FIG. 1 further comprises a sixth fluid port 23 arranged at the second compartment 26 of the first lid 20, the sixth fluid port 23 being closed by a closing means 56 such as a cap. This is advantageous for a symmetric form of the filter device 10 with respect to a middle surface at half-length of the housing 12.

The first group of hollow fibers 40a may preferably comprise more fibers than the second group of hollow fibers 40b. For instance, the first group of hollow fibers 40a may comprise at least 70% of the entire amount of hollow fibers 40 arranged within the housing 12 of the filter device 10.

The filter device 10 may be configured as a dialyser and is applicable for different types of dialysis, for instance in haemodialysis (HD), haemofiltration (HF), haemodiafiltration (HDF).

Figure 2A:
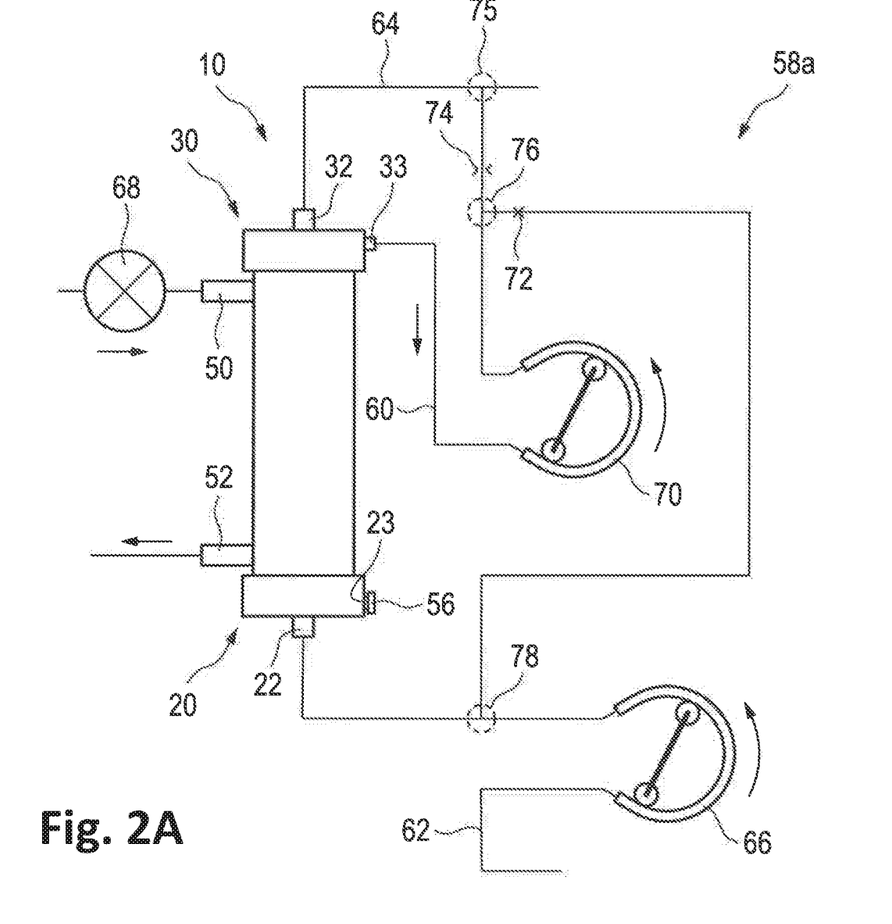
FIG. 2A shows schematically a system according to an embodiment, the system comprising the filter device shown in FIG. 1.

FIG. 2A shows schematically a system 58a for filtration of fluids according to an embodiment. The system 58a comprises a filter device 10 as shown in FIG. 1 and a substitution fluid line 60 for fluidly connecting the third fluid port 33 of the filter device 10 selectively either to the first fluid port 22/arterial line 62 or to the second fluid port 32/venous line 64 depending on if a pre- or post-dilution treatment is desired. The substitution fluid line 60 is arranged outside the housing 12 of the filter device 10.

The system 58a in FIG. 2 further comprises an arterial line 62 for fluidly connecting an arterial side of a patient access to the first fluid port 22 of the filter device 10 and a venous line 64 for fluidly connecting a venous side of the patient access to the second fluid port 32 of the filter device 10. In addition, the system 58a comprises a first pump being an arterial pump 66 for pumping a first fluid into the first fluid port 22. Alternatively or additionally, a venous pump may be provided for draining the first fluid from the second fluid port 32 of the filter device 10. A second pump 68 is provided for pumping a second fluid into the fourth fluid port 50. Alternatively or additionally, a pump may be provided for draining the second fluid from the fifth fluid port 52 of the filter device 10.

As shown in the preferable embodiment of FIG. 2, the substitution fluid line 60 is fluidly connected to the arterial line 62 at a port 78 and to the venous line 64 at another port 75.

Figure 2B:
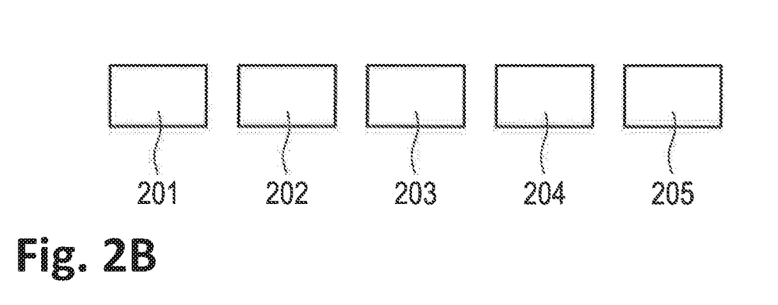
FIG. 2B shows a method for filtration of fluids according to an embodiment using the filter device shown in FIG. 1, in particular using the system shown in FIG. 2A.

FIG. 2B shows a method for filtration of fluids using the filter device 10 shown in FIG. 1, in particular using the system 58a shown in FIG. 2A. In step 201, blood from the arterial side of a patient access is introduced into the filter device 10 through the arterial line 62 and subsequently through the first fluid port 22, wherein this step is preferably facilitated by the arterial pump 66. In step 202, the introduced artery blood is directed from the first lid 20 to the second lid 30 of the filter device 10 via the first compartment 24, the first group of hollow fibers 40a and the second compartment 26 in this order. In step 203, the directed blood is drained from the filter device 10 through the second fluid port 32, wherein this step may be facilitated by a venous pump (not shown).

In step 204, a dialysis fluid is introduced into the filter device 10 through the fourth fluid port 50, wherein this step is preferably facilitated using the inlet dialysis pump 68. In step 205, the introduced dialysis fluid is drained from the filter device 10 through the fifth fluid port 52, wherein this step may be facilitated using an outlet dialysis pump (not shown). After the dialysis fluid has been introduced into the fluid chamber 18 of the filter device 10, a fluid connection between the fourth fluid port 50 and the first and second group of hollow fibers 40a, 40b enables the dialysis fluid to reach the fibers 40a,40b via the fluid chamber 18.

In another step, a third fluid, in particular useful fluids such as substitution fluids, infusion fluids and/or buffer fluids, may be produced by filtering the second fluid (dialysis fluid). The second fluid is preferably filtered into the second group of hollow fibers 40b through the semi-permeable membranes of the fibers 40b. The second fluid may permeate into the internal fluid channels of the second group of hollow fibers 40b through the semi-permeable membranes of these fibers 40b such that the second fluid is thereby filtered. This filtered second fluid is (or may be used as) the third fluid (substitution fluid). Subsequently, the third fluid is preferably drained from the filter device 10 by flowing from the internal channels of the second group of fibers 40b to the third fluid port 33 via the fourth compartment 36 (FIG. 1), before entering the substitution fluid line 60. This is preferably facilitated by the pump 70.

The substitution fluid line 60 may be connected selectively either to the arterial line 62 or to the venous line 64. A pre-dilution mode can be achieved by operating a valve 74 between the venous line 64 and the substitution fluid line 60 in a closed state and by operating a valve 72 between the arterial line 62 and the substitution fluid line 60 in an opened state. In this configuration, the third fluid produced as described above can be pumped from the third fluid port 33 to the port 78 via the opened valve 72. At the port 78, the third fluid is mixed to the blood from the arterial side of the patient access before being introduced to the filter device 10 again.

Further, a post-dilution mode can be achieved by operating the valves 72 and 74 in a reverse manner with respect to the pre-dilution state, i.e. the valve 72 in a closed state and the valve 74 in an opened state. In this configuration, the third fluid produced as described above can be pumped from the third fluid port 33 to the port 75 via the opened valve 74. At the port 75, the third fluid is mixed to the filtered blood from the second fluid port 32 of the filter device 10 before entering the venous side of the patient access.

Figure 3:
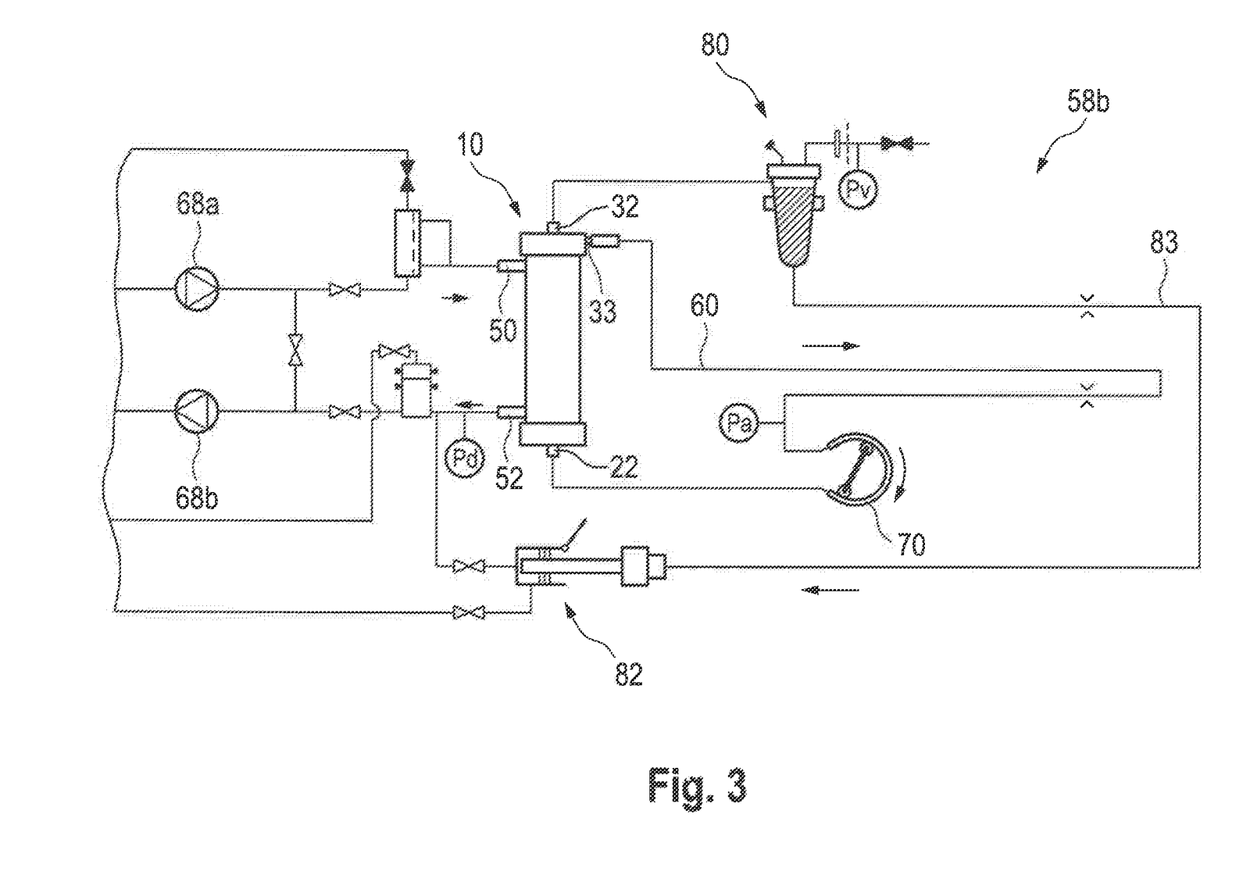
FIG. 3 shows a system according to another embodiment.

FIG. 3 shows schematically a system 58b according to another embodiment. The system 58b comprises a filter device 10 as shown in FIGS. 1-2 and a substitution fluid line 60 as shown in FIG. 2. Further, the system 58b comprises a line 83 for fluidly connecting the second fluid port 32 of the filter device 10 to a waste handling unit 82. The waste handling unit 82 is preferably a waste handling option (WHO) for further processing the waste. Preferably, the line 83 comprises a venous drip chamber 80 for detecting and/or collecting air bubbles, thereby increasing the safety of the system 58b. The venous drip chamber 80 is used during dialysis treatment, but has no function during priming. As shown in FIG. 3, two dialysis pumps 68a, 68b are connected each to one of the fourth and fifth fluid port 50, 52, respectively, wherein the arrows shown at the pumps 68a, 68b indicate the pumping directions.

Figure 4:
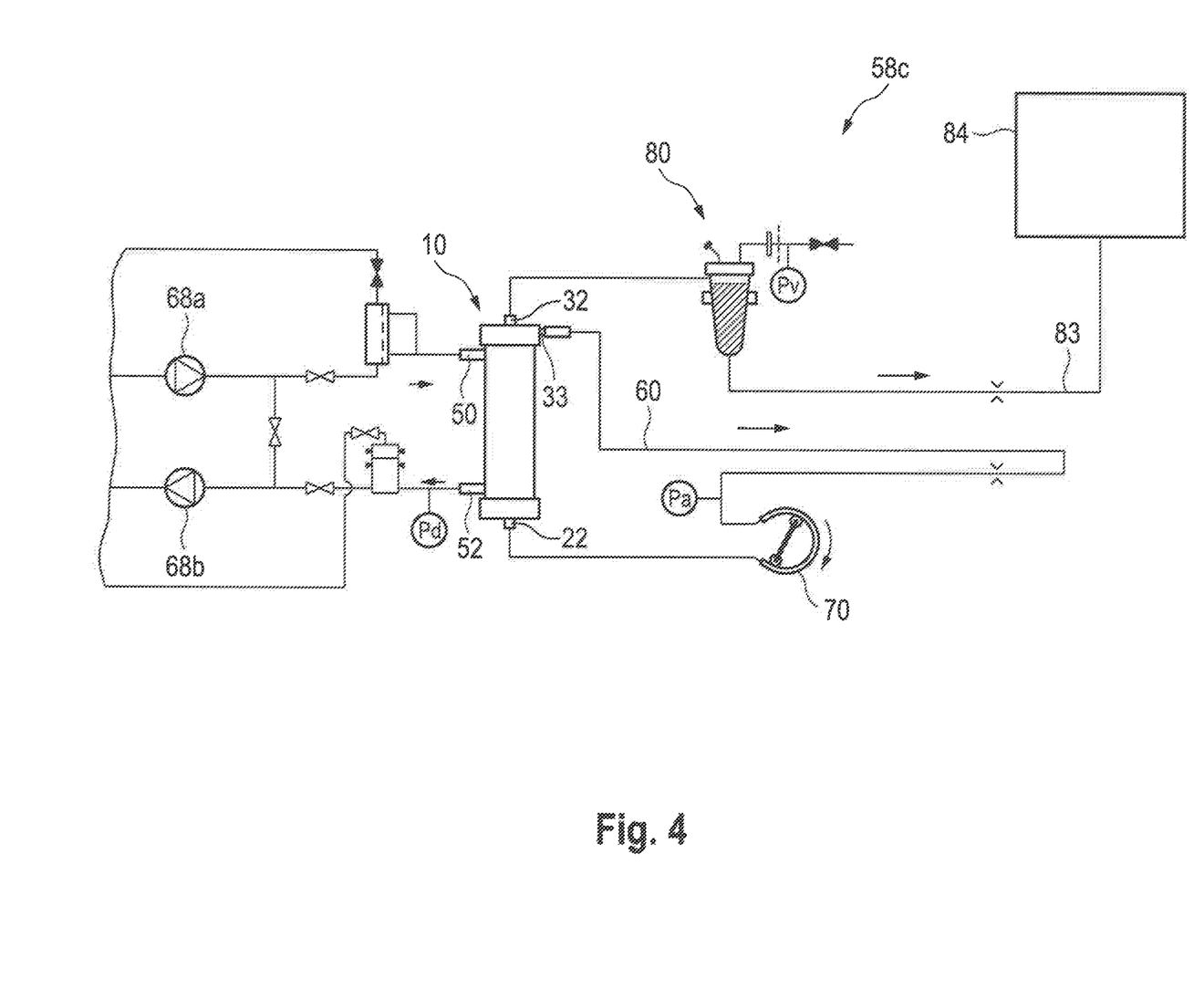
FIG. 4 shows schematically a system according to further embodiment.

FIG. 4 shows schematically a system 58c according to another embodiment. The system 58c is similar to the system 58b shown in FIG. 3, except that the line 83 here is connected not to a waste handling unit, but a waste bag 84.

All systems 58a, 58b, 58c shown in FIGS. 2-4 are preferably configured to contain only one or two additional filters in the dialysis fluid path in addition to the filter device 10. This enables to use only two or three filters in total in the system, including the filter device 10 itself, to perform filtration, in particular to produce substitution fluids by filtering the substitution fluids through these filters.

Hollow fiber membranes which can be used in the device 10 shown in FIGS. 2-4 are so-called high-flux membranes. High-flux membranes are conventional dialysis membranes. They are classified as "high-flux" membranes in distinction to "low-flux" membranes depending on their permeability. High-flux membranes used in devices, such as, for example, the Polyflux® H-series of Gambro, the Revaclear® dialyzers of Gambro and the Ultraflux® EMIC2 or Optiflux® F180NR dialyzer of Fresenius Medical Care have been on the market for several years now. The high-flux membranes used therein are mainly polysulfone or polyethersulfone based membranes and methods for their production have been described, for example, in U.S. Pat. No. 5,891,338 or EP 2 113 298 A1. Another polyphenylene membrane which is known as a high-flux membrane is used in the Phylther® HF 17G filter from Bellco Società unipersonale a r.l. The expression "high-flux membrane(s)" as used herein generally refers to membranes having a MWRO between 5 kDa and 10 kDa and a MWCO between 25 kDa and 65 kDa, as determined by dextran sieving measurements according to Boschetti et al. (Extended characterization of a new class of membranes for blood purification: The high cut-off membranes. Int J Artif Organs 2013; 36(7), 455-463)). Their average pore radius is in the range of from 3.5 to 5.5 nm, wherein the pore size is determined from the MWCO based on dextran sieving coefficients according to Boschetti-de-Fierro et al. (2013). The packing density of the hollow fiber membranes in the device 10 is from 35% to 68%, i.e., the sum of the cross-sectional area of all hollow fiber membranes present in the dialyzer amounts to 35 to 68% of the cross-sectional area of the part of the housing comprising the bundle of semi-permeable hollow fiber membranes. According to one embodiment, the packing density of the hollow fiber membranes in the device 10 is from 45% to 60%. If n hollow fiber membranes are present in the bundle of semi-permeable hollow fiber membranes, $D_F$ is the outer diameter of a single hollow fiber membrane, and $D_H$ is the inner diameter of the part of the dialyzer housing comprising the bundle, the packing density can thus be calculated according to $n*(D_F/D_H)^2$.

The filter device 10 shown in FIG. 1 and the systems 58a, 58b, 58c shown in FIGS. 2-4 may be used to perform priming and/or rinse-back of the filter device 10.

The filter device 10, in particular a dialyser, may normally be delivered in a dry state. In the preparation of dialysis-type treatments, the dialyser is first filled and flown through with an aqueous physiological solution or priming fluid. This process is referred to as dialyser preparation or priming. Such a priming fluid is normally extracted from an external saline bag containing a saline fluid.

Using the filter device 10 or the system 58a, 58b, 58c n, the priming can be done by producing a priming fluid based on the dialysis fluid, using the way to produce the third fluid described above. In particular, the priming fluid can be generated by filtering the third fluid out of the introduced dialysis fluid and by directing the third fluid to enter the first fluid port 22 via the substitution fluid line 60. The pump 70 may facilitates this process. The dialysis fluid is normally not suitable to be used directly as priming fluid due to the contaminants contained in it. The filter device 10 or the system 58a, 58b, 58c therefore enable to produce a priming fluid and to perform priming of the filter device 10 and/or the hollow fibers 40 without using any saline bag.

The process of rinse-back is performed after filtration of fluids, in particular after the dialysis-type treatment has almost been completed. The remainder of filtered fluid, e.g. blood, needs to be pumped into the venous line to enter the venous side of the patient access. This is normally done using a saline fluid from a saline bag as rinse-back fluid.

Using the filter device 10 or the system 58a, 58b, 58c, the rinse-back can be done by producing a rinse-back fluid based on the dialysis fluid, using the way to produce the third fluid described above. In particular, the rinse-back fluid can be generated by filtering the third fluid out of the introduced dialysis fluid and by directing the third fluid to enter the first fluid port 22 via the substitution fluid line 60. This process may be facilitated by the pump 70. The dialysis fluid is normally not suitable to be used directly as rinse-back fluid due to the contaminants contained in it. The filter device 10 or the system 58a, 58b, 58c therefore enable to produce a rinse-back fluid and to perform priming of the filter device 10 and/or the hollow fibers 40 without using any saline bag.

Figure 5:
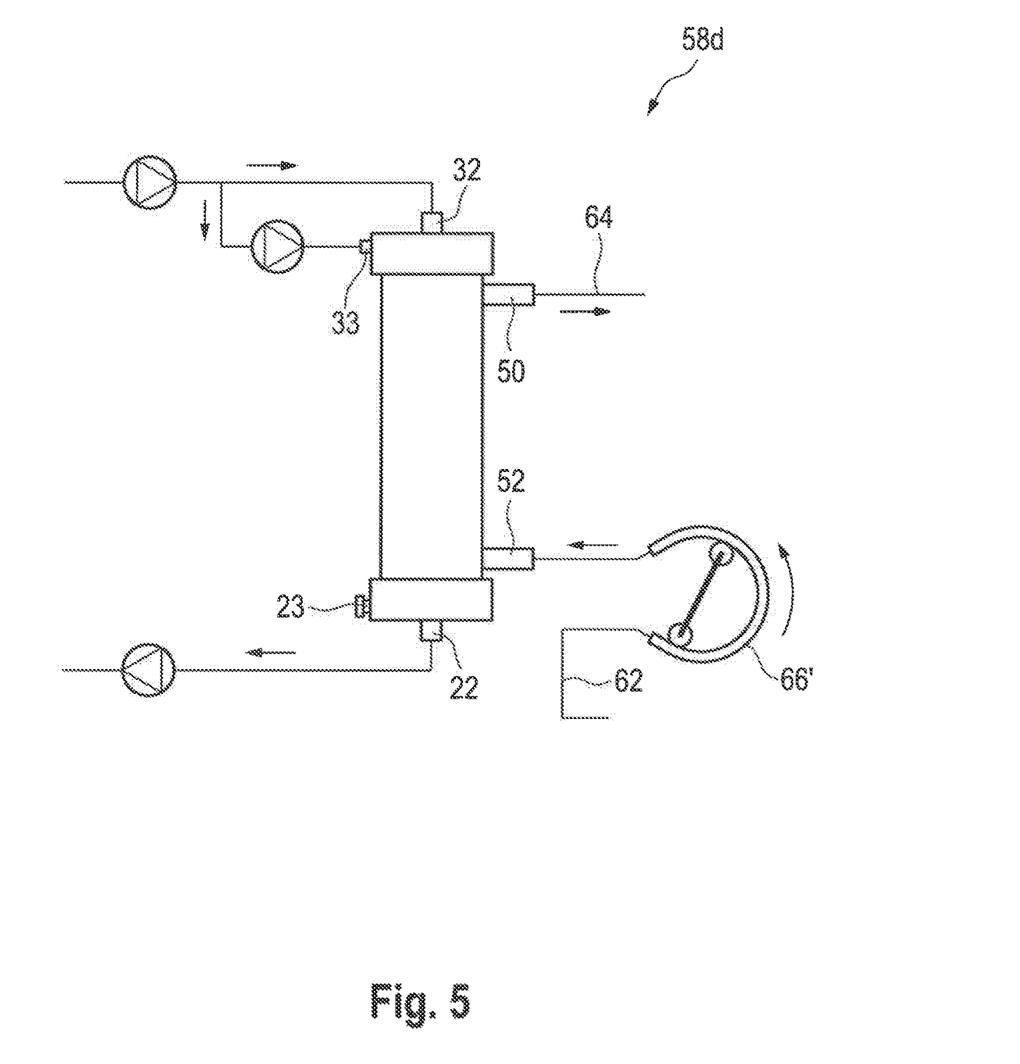
FIG. 5 shows schematically a system according to a still further embodiment.

A still further embodiment of a system 58d including the device 10 is schematically shown in FIG. 5. This embodiment shall, inter alia, illustrate that the device 10 is not restricted to the flow directions described above with reference to the systems 58a, 58b, 58c according to the embodiments shown in FIGS. 2-4. Hence could any of the fluid ports 50 and 52 be an inlet while the other is an outlet. The same is true for the fluid ports 22 and 32. Moreover, the first fluid is not restricted to flow inside the first group of fibers 40a. It could equally well flow outside the fibers 40a, 40b while the second fluid is instead flowing inside the fibers 40a. In such a setting the substitution fluid is created by instead introducing dialysis fluid into port 33 or 23 and let it be filtered when passing from the interior to the exterior of the second group of fibers 40b. In a dialysis treatment situation this means that the substitution fluid is mixed with the blood inside the dialyzer 10.

In the embodiment schematically illustrated in FIG. 5, blood from the arterial side of the patient access is pumped by pump 66' from the arterial line 62 into the fifth fluid port 52. The fourth fluid port 50 is connected to the venous line 64. The blood thus flows through the fluid chamber 18 of the device 10 outside the the fibers 40a, 40b. A part of the dialysis fluid in this embodiment enters the device 10 at the second fluid port 32, flows inside the first group of fibers 40a, and leaves the device 10 again at the first fluid port 22. The other part of the dialysis fluid enters the device 10 at the third fluid port 33 and flows via the fourth compartment 36 into the interior of the second group of hollow fibers 40b. Substitution fluid is created by let this part of the dialysis fluid be filtered when passing from the interior to the exterior of the second group of fibers 40b. The substitution fluid may then be mixed with the blood in the fluid chamber 18 outside of the fibers 40a, 40b, and may then leave the device 10 together with the blood at the fourth fluid port 50.

If the device 10 is operated in the way shown in FIG. 5, a special type of hollow fiber membranes is preferably used. Hollow fiber membranes which can be used in for the embodiment shown in FIG. 5 are membranes wherein the blood is in contact with the outside of the membrane and the dialysis fluid is channeled through the lumen of the hollow fibers. Such membranes are known in the art and have been described, for example, in WO 2008/046779 A1. Further considerations as concerns the use of membranes having their selective layer on the outside have been provided for in US 2015/0314057 A1. Packing densities in this case are calculated as described before and will advantageously lie in the range of from 30% to 60%.

It follows a list of further embodiments:
1. Filter device for filtration of fluids, comprising:
   a housing having a first end and a second end and defining a fluid chamber extending between the first end and the second end;
   a first lid provided at the first end of the housing and comprising a first fluid port, a first compartment, a second compartment and a first internal separating wall separating the first compartment from the second compartment;

a second lid provided at the second end of the housing and comprising a second fluid port, a third fluid port, a third compartment, a fourth compartment and a second internal separating wall separating the third compartment from the fourth compartment;

a plurality of hollow fibers arranged within the housing, wherein each of the plurality of hollow fibers comprises a semi-permeable membrane and defines a fluid channel extending longitudinally through an interior of the respective hollow fiber;

a first sealing means which separates the fluid chamber from the first and the second compartment, the first sealing means having a first longitudinal end facing away from the second lid;

a second sealing means which separates the fluid chamber from the third and the fourth compartment, the second sealing means having a second longitudinal end facing away from the first lid;

a fourth fluid port and a fifth fluid port both provided at the fluid chamber and located between the first longitudinal end of the first sealing means and the second longitudinal end of the second sealing means;

wherein the first fluid port is arranged at the first compartment, wherein the second fluid port is arranged at the third compartment, wherein the third fluid port is arranged at the fourth compartment, wherein the plurality of hollow fibers comprise a first group of fibers and a second group of fibers, wherein each hollow fiber of the first group of fibers extends from the first compartment through the fluid chamber to the third compartment, and wherein each hollow fiber of the second group of fibers extends from the second compartment through the fluid chamber to the fourth compartment, and wherein the fourth and the fifth fluid port are fluidly connected to one another and in fluidic communication with an exterior of the plurality of hollow fibers via the fluid chamber.

2. The filter device according to embodiment 1, wherein the fourth and the fifth fluid port are in direct fluid connection to the fluid chamber, the direct fluid connection being located between the first longitudinal end of the first sealing means and the second longitudinal end of the second sealing means.

3. The filter device according to embodiment 1 or 2, wherein the fluid chamber is spatially confined by an inner wall of the housing, the first sealing means and the second sealing means.

4. The filter device according to any of embodiments 1-3, wherein the first compartment is fluidly isolated from the second compartment by means of the first sealing means and the first internal separating wall, and/or wherein the third compartment is fluidly isolated from the fourth compartment by means of the second sealing means and the second internal separating wall.

5. The filter device according to any of embodiments 1-4, wherein the first and/or the second sealing means comprises a potting compound for receiving the first and/or the second group of hollow fibers.

6. The filter device according to any of embodiments 1-5, further comprising a sixth fluid port arranged at the second compartment of the first lid, the sixth fluid port being closed by a closing means.

7. The filter device according to any of embodiments 1-6, wherein the first group of hollow fibers comprise more fibers than the second group of hollow fibers.

8. The filter device according to embodiment 7, wherein the first group of hollow fibers comprise at least 70% of the plurality of hollow fibers.

9. The filter device according to any of embodiments 1-8, wherein the fluid chamber comprises a part that has a substantially cylindrical shape.

10. System for filtration of fluids, comprising the filter device according to any of embodiments 1-9, further comprising a substitution fluid line for fluidly connecting the third fluid port selectively to the first fluid port of the filter device or to the second fluid port of the filter device, the substitution fluid line being arranged outside the housing of the filter device.

11. The system according to embodiment 10, further comprising:

an arterial line for fluidly connecting an arterial side of a patient access to the first fluid port of the filter device;

a venous line for fluidly connecting a venous side of the patient access to the second fluid port of the filter device;

a first pump for pumping a first fluid into the first fluid port and/or for draining the first fluid from the second fluid port of the filter device; and a second pump for pumping a second fluid into the fourth fluid port and/or for draining the second fluid from the fifth fluid port of the filter device.

12. The system according to embodiment 11, wherein the substitution fluid line is fluidly connected to the arterial line and/or the venous line.

13. The system according to any of embodiments 10-12, further comprising a line for fluidly connecting the second fluid port of the filter device to a waste handling unit and/or a waste bag.

14. The system according to any of embodiments 10-13, further containing only one or two additional filters in addition to the filter device.

15. A method for filtration of fluids using the filter device according to any of embodiments 1-9, comprising the steps of:

introducing a first fluid into the filter device through the first fluid port;

directing the first fluid from the first lid to the second lid via the first compartment, the fluid channels in the interior of the first group of hollow fibers, and the second compartment;

draining the first fluid from the filter device through the second fluid port;

introducing a second fluid into the filter device through the fourth fluid port;

draining a first part of the second fluid from the filter device through the fifth fluid port;

filtering a second part of the second fluid by guiding it from the fourth fluid port via the fluid chamber to the exterior of the second group of hollow fibers, through the permeable semi-permeable membranes of the second group of hollow fibers into the fluid channels in the interior of the second group of hollow fibers (40*b*) and to the third fluid port; and draining the filtered second part of the second fluid from the filter device through the third fluid port.

What is claimed is:

1. System for filtration of fluids, comprising a filter device for filtration of fluids, wherein the filter device comprises:

a housing having a first end and a second end and defining a fluid chamber extending between the first end and the second end;

a first lid provided at the first end of the housing and comprising a first fluid port, a first compartment, a second compartment and a first internal separating wall separating the first compartment from the second compartment;

a second lid provided at the second end of the housing and comprising a second fluid port, a third fluid port, a third compartment, a fourth compartment and a second internal separating wall separating the third compartment from the fourth compartment;

a plurality of hollow fibers arranged within the housing, wherein each of the plurality of hollow fibers comprises a semi-permeable membrane and defines a fluid channel extending longitudinally through an interior of the respective hollow fiber;

a first sealing means which separates the fluid chamber from the first and the second compartment, the first sealing means having a first longitudinal end facing away from the second lid;

a second sealing means which separates the fluid chamber from the third and the fourth compartment, the second sealing means having a second longitudinal end facing away from the first lid; and a fourth fluid port and a fifth fluid port both provided at the fluid chamber and located between the first longitudinal end of the first sealing means and the second longitudinal end of the second sealing means;

wherein the first fluid port is arranged at the first compartment, wherein the second fluid port is arranged at the third compartment, wherein the third fluid port is arranged at the fourth compartment, wherein the plurality of hollow fibers comprise a first group of fibers and a second group of fibers, wherein each hollow fiber of the first group of fibers extends from the first compartment through the fluid chamber to the third compartment and fluidly connects the first compartment with the third compartment via the fluid channels extending through the interior of each hollow fiber of the first group of fibers, and wherein each hollow fiber of the second group of fibers extends from the second compartment through the fluid chamber to the fourth compartment and fluidly connects the second compartment with the fourth compartment via the fluid channels extending through the interior of each hollow fiber of the second group of fibers, wherein the fourth and the fifth fluid port are fluidly connected to one another and both in fluidic communication with an exterior of both the hollow fibers of the first and the second group of fibers via the fluid chamber, and wherein the system further comprises a substitution fluid line which is configured to be switchable between a pre-dilution mode, in which the third fluid port is fluidly connected to the first fluid port of the filter device, and a post-dilution mode, in which the third fluid port is fluidly connected to the second fluid port of the filter device, the substitution fluid line being arranged outside the housing of the filter device.

2. The system according to claim 1, wherein the substitution fluid line comprises a first valve, which is arranged in a fluidic connection between the third fluid port and the first fluid port, and a second valve, which is arranged in a fluidic connection between the third fluid port and the second fluid port, wherein in the pre-dilution mode the first valve is operated to be in an opened state and the second valve is operated to be in a closed state, and wherein in the post-dilution mode the first valve is operated to be in a closed state and the second valve is operated to be in an opened state.

3. The system according to claim 1, wherein the fourth and the fifth fluid port are in direct fluid connection to the fluid chamber, the direct fluid connection being located between the first longitudinal end of the first sealing means and the second longitudinal end of the second sealing means.

4. The system according to claim 1, wherein the fluid chamber is spatially confined by an inner wall of the housing, the first sealing means and the second sealing means.

5. The system according to claim 1, wherein the first compartment is fluidly isolated from the second compartment by means of the first sealing means and the first internal separating wall, and/or wherein the third compartment is fluidly isolated from the fourth compartment by means of the second sealing means and the second internal separating wall.

6. The system according to claim 1, wherein the first and/or the second sealing means comprises a potting compound for receiving the first and/or the second group of hollow fibers.

7. The system according to claim 1, further comprising a sixth fluid port arranged at the second compartment of the first lid, the sixth fluid port being closed by a closing means.

8. The system according to claim 1, wherein the first group of hollow fibers comprise more fibers than the second group of hollow fibers.

9. The system according to claim 8, wherein the first group of hollow fibers comprise at least 70% of the plurality of hollow fibers.

10. The system according to claim 1, wherein the fluid chamber comprises a part that has a substantially cylindrical shape.

11. The system according to claim 1, further comprising:
an arterial line for fluidly connecting an arterial side of a patient access to the first fluid port of the filter device;
a venous line for fluidly connecting a venous side of the patient access to the second fluid port of the filter device;
a first pump for pumping a first fluid into the first fluid port and/or for draining the first fluid from the second fluid port of the filter device; and
a second pump for pumping a second fluid into the fourth fluid port and/or for draining the second fluid from the fifth fluid port of the filter device.

12. The system according to claim 11, wherein the substitution fluid line is fluidly connected to the arterial line and/or the venous line.

13. The system according to claim 1, further comprising a line for fluidly connecting the second fluid port of the filter device to a waste handling unit and/or a waste bag.

14. The system according to claim 1, further containing only one or two additional filters in addition to the filter device.

15. A method for filtration of fluids using a filter device which comprises:
a housing having a first end and a second end defining a fluid chamber extending between the first end and the second end;
a first lid provided at the first end of the housing and comprising a first fluid port, a first compartment, a second compartment and a first internal separating wall separating the first compartment from the second compartment;

a second lid provided at the second end of the housing and comprising a second fluid port, a third fluid port, a third compartment, a fourth compartment and a second internal separating wall separating the third compartment from the fourth compartment;

a plurality of hollow fibers arranged within the housing, wherein each of the plurality of hollow fibers comprises a semi-permeable membrane and defines a fluid channel extending longitudinally through an interior of the respective hollow fiber;

a first sealing means which separates the fluid chamber from the first and the second compartment, the first sealing means having a first longitudinal end facing away from the second lid;

a second sealing means which separates the fluid chamber from the third and the fourth compartment, the second sealing means having a second longitudinal end facing away from the first lid; and a fourth fluid port and a fifth fluid port both provided at the fluid chamber and located between the first longitudinal end of the first sealing means and the second longitudinal end of the second sealing means;

wherein the first fluid port is arranged at the first compartment, wherein the second fluid port is arranged at the third compartment, wherein the third fluid port is arranged at the fourth compartment, wherein the plurality of hollow fibers comprise a first group of fibers and a second group of fibers, wherein each hollow fiber of the first group of fibers extends from the first compartment through the fluid chamber to the third compartment and fluidly connects the first compartment with the third compartment via the fluid channels extending through the interior of each hollow fiber of the first group of fibers, and wherein each hollow fiber of the second group of fibers extends from the second compartment through the fluid chamber to the fourth compartment and fluidly connects the second compartment with the fourth compartment via the fluid channels extending through the interior of each hollow fiber of the second group of fibers, wherein the fourth and the fifth fluid port are fluidly connected to one another and both in fluidic communication with an exterior of both the hollow fibers of the first and the second group of fibers via the fluid chamber, and wherein using the filter device comprises the steps of:

introducing a first fluid into the filter device through the first fluid port;

directing the first fluid from the first lid to the second lid via the first compartment, the fluid channels in the interior of the first group of hollow fibers, and the third compartment;

draining the first fluid from the filter device through the second fluid port;

introducing a second fluid into the filter device through the fourth fluid port;

draining a first part of the second fluid from the filter device through the fifth fluid port;

filtering a second part of the second fluid by guiding it from the fourth fluid port via the fluid chamber to the exterior of the second group of hollow fibers, through the semi-permeable membranes of the second group of hollow fibers into the fluid channels in the interior of the second group of hollow fibers and to the third fluid port; and draining the filtered second part of the second fluid from the filter device through the third fluid port.

16. The method according to claim 15, further comprising the steps of:

providing a substitution fluid line which is arranged outside the housing of the filter device; and switching the substitution fluid line between a pre-dilution mode, in which the substitution fluid line fluidly connects the third fluid port to the first fluid port of the filter device, and a post-dilution mode, in which the substitution fluid line fluidly connects the third fluid port to the second fluid port of the filter device.

* * * * *